US012721985B2

(12) United States Patent
Rhee et al.

(10) Patent No.: US 12,721,985 B2
(45) Date of Patent: Sep. 1, 2026

(54) MICRONEEDLE PATCH SYSTEM FOR TRANSDERMAL DRUG DELIVERY

(71) Applicant: INDUSTRY-ACADEMIC COOPERATION FOUNDATION GYEONGSANG NATIONAL UNIVERSITY, Jinju-si (KR)

(72) Inventors: Yun Seok Rhee, Jinju-si (KR); Sangbyeong Song, Jinju-si (KR); Jaemin Lee, Jinju-si (KR); Chanwoo Song, Jinju-si (KR); Inhwan Noh, Jinju-si (KR)

(73) Assignee: INDUSTRY-ACADEMIC COOPERATION FOUNDATION GYEONGSANG NATIONAL UNIVERSITY, Jinju-Si (KR)

(*) Notice: Subject to any disclaimer, the term of this patent is extended or adjusted under 35 U.S.C. 154(b) by 481 days.

(21) Appl. No.: 18/547,020

(22) PCT Filed: Jan. 28, 2022

(86) PCT No.: PCT/KR2022/001550

§ 371 (c)(1), (2) Date: Aug. 18, 2023

(87) PCT Pub. No.: WO2022/177205

PCT Pub. Date: Aug. 25, 2022

(65) Prior Publication Data

US 2025/0018162 A1 Jan. 16, 2025

(30) Foreign Application Priority Data

Feb. 18, 2021 (KR) ........................ 10-2021-0021611

(51) Int. Cl.

| | |
|---|---|
| ***A61M 37/00*** | (2006.01) |
| ***A61K 9/00*** | (2006.01) |

(52) U.S. Cl.

CPC ....... *A61M 37/0015* (2013.01); *A61K 9/0021* (2013.01); *A61M 2037/0023* (2013.01)

(58) Field of Classification Search

CPC .................. A61M 37/0015; A61M 2037/0023

See application file for complete search history.

(56) References Cited

U.S. PATENT DOCUMENTS

| | | | | |
|---|---|---|---|---|
| 2008/0051695 A1* | 2/2008 | Xu | .................... | A61M 37/0015 604/22 |
| 2020/0009364 A1* | 1/2020 | Amir | .................... | A61K 9/0021 |

(Continued)

FOREIGN PATENT DOCUMENTS

| | | |
|---|---|---|
| JP | 5460538 B2 | 4/2014 |
| JP | 2016528971 A | 9/2016 |

(Continued)

OTHER PUBLICATIONS

Translation of KR101878414 (Year: 2026).*

(Continued)

*Primary Examiner* — Dung T Ulsh

(74) *Attorney, Agent, or Firm* — Fredrikson & Byron, P.A.

(57) ABSTRACT

The present invention relates to a microneedle patch system for continuously administering a large amount of drug to the skin. A microneedle patch provided by one aspect of the present invention may have increased drug content per unit area (1 $cm^2$) to maximum of 100 mg unlike existing microneedles and thus has a higher drug content per unit area than an existing transdermal absorption agent, and is capable of delivering the drug into the body for a short time (within 24 hours) and a long time (approximately three days or more) via micropores formed by means of microneedles.

13 Claims, 5 Drawing Sheets

(56) References Cited

U.S. PATENT DOCUMENTS

2020/0289330 A1* 9/2020 Spector ............ A61F 13/00051
2022/0249820 A1* 8/2022 Wanichwecharungruang ............ A61M 37/0015

FOREIGN PATENT DOCUMENTS

| | | | | |
|---|---|---|---|---|
| JP | 2016189844 | * | 11/2016 | |
| JP | 2016189844 A | | 11/2016 | |
| KR | 101549086 | | 9/2015 | |
| KR | 1020150138646 A | | 12/2015 | |
| KR | 1020160095576 A | | 8/2016 | |
| KR | 101878414 B1 | * | 7/2018 | .............. A61P 37/08 |
| KR | 1020190123642 A | | 11/2019 | |

OTHER PUBLICATIONS

Translation of JP2016189844 (Year: 2026).*

International Search Report and Written Opinion of the International Application No. PCT/KR2022/001550, mailed May 30, 2022, 8 pg.

Formation and Closure of Microchannels in Skin Following Microporation, Pharm Res (2011) 28:82-94.

* cited by examiner

FIG. 2

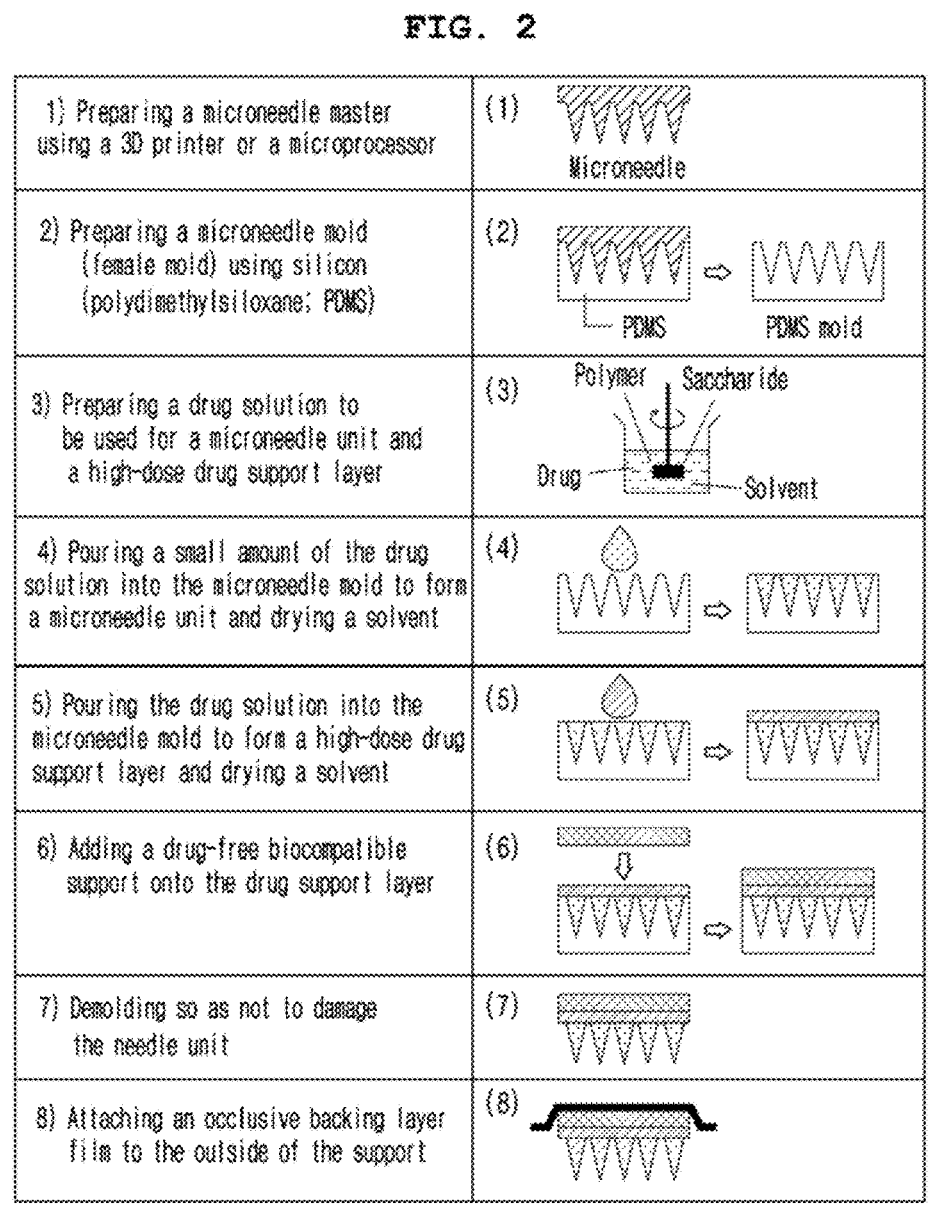

| Step | Illustration |
| --- | --- |
| 1) Preparing a microneedle master using a 3D printer or a microprocessor | (1) Microneedle |
| 2) Preparing a microneedle mold (female mold) using silicon (polydimethylsiloxane; PDMS) | (2) PDMS ⇨ PDMS mold |
| 3) Preparing a drug solution to be used for a microneedle unit and a high-dose drug support layer | (3) Polymer, Saccharide, Drug, Solvent |
| 4) Pouring a small amount of the drug solution into the microneedle mold to form a microneedle unit and drying a solvent | (4) |
| 5) Pouring the drug solution into the microneedle mold to form a high-dose drug support layer and drying a solvent | (5) |
| 6) Adding a drug-free biocompatible support onto the drug support layer | (6) |
| 7) Demolding so as not to damage the needle unit | (7) |
| 8) Attaching an occlusive backing layer film to the outside of the support | (8) |

FIG. 3
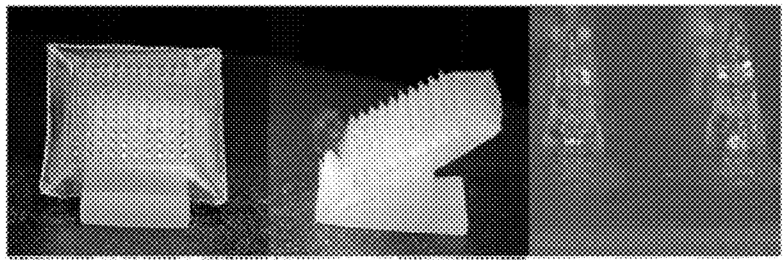
FIG. 4
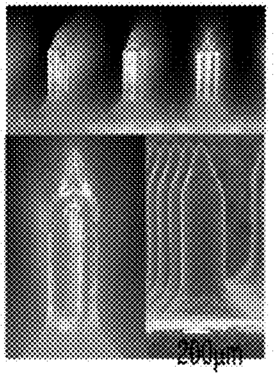
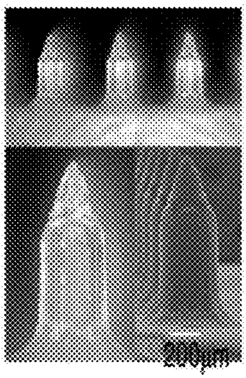
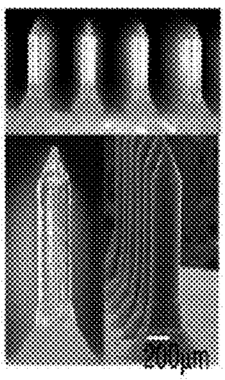

FIG. 5
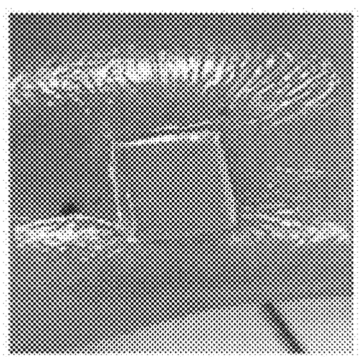
Shape of a film immediately after attachment to the skin
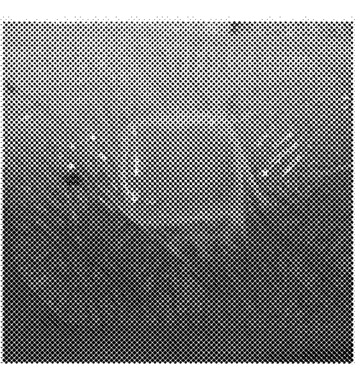
Shape of a gelated film after a certain period of time
FIG. 6
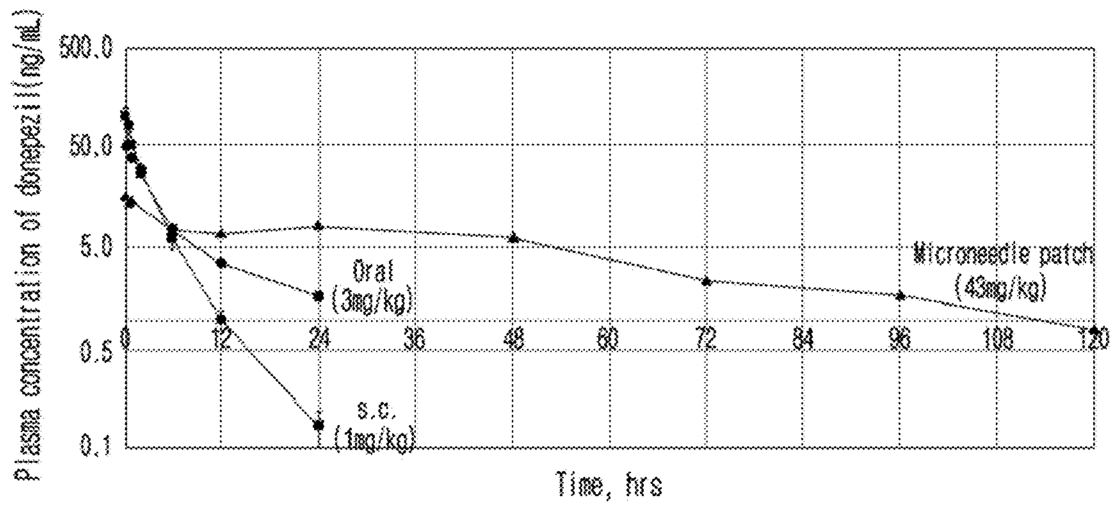

MICRONEEDLE PATCH SYSTEM FOR TRANSDERMAL DRUG DELIVERY

CROSS-REFERENCES TO RELATED APPLICATION

This patent application is a 35 U.S.C. 371 national phase filing from International Application No. PCT/KR2022/001550, filed Jan. 28, 2022, which claims the benefit of priority under 35 U.S.C. § 119 from Korean Patent Application 10-2021-0021611 filed on Feb. 18, 2021 the contents of which are incorporated herein by reference.

BACKGROUND OF THE INVENTION

1. Field of the Invention

The present invention relates to a microneedle patch system for continuously administering a large amount of drug to the skin.

2. Description of the Related Art

The previously developed microneedle drug delivery system was to coat microneedles with drugs or manufacture microneedles with soluble microneedles including drugs (Patent Reference 1, Patent Publication No. 2016-189844). The disadvantage of the two systems is that the amount of drug that can be coated or the amount of drug that can be included in the dissolving type microneedle is very limited, so it is difficult or almost impossible to load more than 1 mg of drug. Therefore, the types of drugs that can be applied with the microneedle are also very limited, so there is great difficulty in replacing injections or existing transdermal drug delivery systems.

In addition to the previous two strategies, there is a “poke and patch” method. In this method, microneedles without drugs are first applied to the skin to create micropores, and then liquids, creams, or patches containing drugs are applied to the pores to increase the skin permeability of the drugs. The main disadvantage of this method that the micropores are only open for a limited time, so the delivery of the active substance stops prematurely. In general, it is known that the barrier function of the skin at the microneedle treatment site is restored within 3 to 4 hours, and the microchannel is closed within 15 hours after being punctured. However, there is a report that if the skin where the micropores were created is occluded, the micropores will remain open fox 72 hours (Non-Patent Reference 1, Formation and Closure of Microchannels in Skin Following Microporation, Pharm Res (2011) 28:82-94, doi: 10.1007/s11095-010-0122-x). In order to apply this to transdermal drug delivery, it is necessary to go through a complicated procedure of applying microneedles to the skin, removing the microneedles, applying a formulation containing drugs to the skin again, and then occluding the skin. It is very inconvenient and practically difficult for patients to generally apply this continuous process reproducibly.

In one aspect of the present invention, a microneedle patch system capable of delivering a large amount of drug through a microneedle is provided by improving the difficulties that previously reported microneedle strategies have not overcome.

SUMMARY OF THE INVENTION

It is an object of the present invention in one aspect to provide a microneedle patch, which has an increased drug content per unit area (1 $cm^2$) to maximum of 100 mg unlike existing microneedles and thus has a higher drug content per unit area than an existing transdermal absorption agent, and is capable of delivering the drug into the body for a short time (within 24 hours) and a long time (approximately three days or more) via micropores formed by means of microneedles.

To achieve the above object, in one aspect of the present invention, a microneedle patch comprising the following components is provided:

- a microneedle comprising a drug;
- a drug support layer supporting the microneedle on one surface and containing a drug;
- a support provided in contact with a surface opposite to the surface of the drug support layer on which the microneedle is supported and not containing a drug; and
- an occlusive backing layer film provided in contact with a surface opposite to the surface of the support to which the drug support layer is in contact, wherein the occlusive backing layer film further includes an adhesive layer that covers the contact support surface and is extended to be directly attached to the skin.

ADVANTAGEOUS EFFECT

A microneedle patch provided by one aspect of the present invention may have increased drug content per unit area (1 $cm^2$) to maximum of 100 mg unlike existing microneedles and thus has a higher drug content per unit than an existing transdermal absorption agent, and is capable of delivering the drug into the body for a short time (within 24 hours) and a long time (approximately three days or more) via micropores formed by means of microneedles.

BRIEF DESCRIPTION OF THE DRAWINGS

FIG. 2 is a schematic diagram showing the manufacturing process of a microneedle patch system provided in one aspect of the present invention.

FIG. 3 is a set of photographs showing the microneedle and the drug support layer prepared to contain 100 mg of donepezil hydrochloride according to Example 1.

FIG. 4 is a set of photographs showing the microneedle prepared to contain 10 mg of celecoxib according to Example 4.

FIG. 5 is a set of photographs showing the state of attaching a film made of a polymer material and saccharides to the skin (left) and the state of a gelated film after a certain period of time (right).

FIG. 6 is a graph showing the results of comparing the drug blood concentration patterns in rats after administration of 3 mg/kg of donepezil orally, 1 mg/kg of donepezil subcutaneously, or 43 mg/kg of donepezil using a microneedle patch prepared in an embodiment.

DESCRIPTION OF THE PREFERRED EMBODIMENTS

Figure 1:
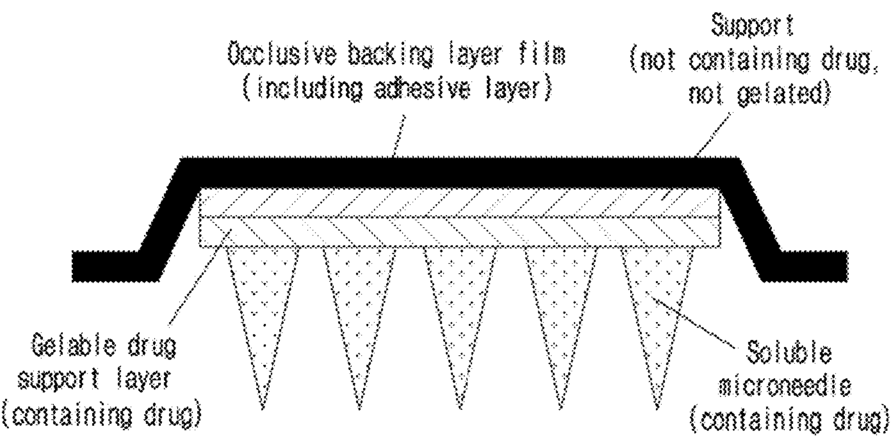
FIG. 1 is a diagram showing the configuration of a microneedle patch system provided in one aspect of the present invention.

Hereinafter, the present invention is described in detail. The embodiments of this invention can be modified in various other forms, and the scope of the present invention is not limited to the embodiments described below. It is well understood by those in the art who has the average knowledge on this field that the embodiments of the present invention are given to explain the present invention more precisely.

In addition, the "inclusion" of an element throughout the specification does not exclude other elements, but may include other elements, unless specifically stated otherwise.

In one aspect of the present invention, microneedle patch comprising the following components is provided:

a microneedle comprising a drug;

a drug support layer supporting the microneedle on one surface and containing a drug;

a support provided in contact with a surface opposite to the surface of the drug support layer on which the microneedle is supported and not containing a drug; and an occlusive backing layer film provided in contact with a surface opposite to the surface of the support to which the drug support layer is in contact, wherein the occlusive backing layer film further includes an adhesive layer that covers the contact support surface and is extended to be directly attached to the skin.

When the microneedle patch system proposed in this invention is applied to the skin, microneedles including drugs create micropores in the skin, and the drug contained in the soluble microneedles diffuses through the micropores, and the drug is quickly delivered into the body. In addition, the drug support layer containing a high-dose drug that was supporting the microneedles absorbs moisture evaporating from the skin and gelates to form a reservoir for the drug, and the drug is continuously delivered into the body through the micropores formed by the microneedles. If the thickness of the gelable drug support layer containing the drug is thin or the strength is not sufficient, a support that reinforces the mechanical strength of the patch system is required, which serves to support the microneedle to uniformly penetrate the skin. The occlusive backing layer film located at the outermost part of the microneedle patch system functions to ensure that the patch system is well fixed to the skin, and at the same time prevents loss of moisture evaporating from the skin, promotes gelation of the support layer, and blocks external microorganisms and foreign substances to prevent microbial infection and contamination of micropores.

Hereinafter, the components constituting the microneedle patch provided in one aspect of the present invention will be described in detail for each component.

(microneedle) The microneedle can invasively penetrate the skin and release the drug as it dissolves within the skin. That is, the microneedle is preferably soluble and can be formed of a mixture of at least one selected from the group consisting of hyaluronic acid, polyvinylpyrrolidone (PVP), polyvinyl alcohol (PVA), and saccharide. In this case, the saccharide can be at least one selected from the group consisting of monosaccharides, disaccharides, and polysaccharides. More specifically, the monosaccharide is at least one selected from the group consisting of fructose, galactose, glucose, and mannose; the disaccharide is at least one selected from the group consisting of sucrose, lactose, maltose, trehalose, turanose and cellobiose; and the polysaccharide is at least one selected from the group consisting of dextran, diethylamino ethyl-dextran, dextrin, cellulose and β-glucans. The microneedle may be one or more shapes selected from the group consisting of a circular cone shape, a quadrangular pyramid shape, and a triangular pyramid shape, but not always limited thereto.

(drug support layer) The drug support layer is gelated by moisture released from the skin, and the drug contained in the drug support layer can be released due to the gelation of the drug support layer. The drug released due to the gelation of the drug support layer is absorbed into the body through the micropores in the skin formed by microneedles. The drug support layer can be formed of a mixture of at least one selected from the group consisting of hyaluronic acid, polyvinylpyrrolidone (PVP), polyvinyl alcohol (PVA), sodium carboxymethyl cellulose (NaCMC), poloxamer, carbomer, hypromellose, hydroxypropyl cellulose (HPC), hydroxyethyl cellulose (HEC), sodium alginate, Saccharide, glycerin, propylene glycol, polyethylene glycol 400, and sorbitol (SB). The material and type forming the microneedle may be the same or different.

(support) The support serves to reinforce the mechanical strength of the patch system when the thickness of the drug support layer is thin or the strength is insufficient, and serves to support the microneedles to penetrate the skin uniformly. The support is a biocompatible material and can be manufactured using polymers, ceramics, metals, and the like. Examples of the biocompatible material include materials containing at least one selected from the group consisting of hyaluronic acid, alginic acid, pectin, carrageenan, chondroitin (sulfate), dextran (sulfate), chitosan, polylysine, collagen, gelatin, carboxymethyl chitin, fibrin, agarose, pullulan polylactide, polyglycolide (PGA), polylactide-glycolide copolymer (PLGA), polyanhydride, polyorthoester, polyetherester, polycaprolactone, polyesteramide, poly(butyric acid), poly(valeric acid), polyurethane, polyacrylate, ethylene-vinylacetate polymer, acryl-substituted cellulose acetate, non-degradable polyurethane, polystyrene, polyvinylchloride, polyvinyl fluoride, poly(vinyl imidazole), chlorosulphonatepolyolefins, polyethylene oxide, polyvinylpyrrolidone (PVP), polyethylene glycol (PEG), polymethacrylate, hydroxypropylmethylcellulose (HPMC), ethyl cellulose (EC), hydroxypropyl cellulose (HPC), carboxymethyl cellulose, cyclodextrin, copolymers of monomers forming these polymers and cellulose. In Examples to be described later, polyvinylpyrrolidone (PVP) was used.

(occlusive backing layer film) The occlusive backing layer film may be semi-permeable or moisture-proof to moisture released from the skin. That is, the occlusive backing layer film may prevent loss of moisture released from the skin to control or promote gelation of the drug support layer. In human skin, moisture is evaporated at a rate of 240-1,920 g/m$^2$ per 24 hours, and if there is a wound, moisture is evaporated at a rate of about 4,800 g/m$^2$. The occlusive backing layer film prevents loss of moisture evaporated from the skin, so that the micropores of the skin formed by the microneedle can be kept open while the microneedle patch is attached to the skin. In the case of the prior art, the micropores of the skin formed by the microneedle are open only for a limited time (generally, the microneedle treated area begins to recover the barrier properties of the skin within 3 to 4 hours), so that the delivery of the active substance is stopped early. On the other hand, in the case of the present invention, when the skin wherein the micropores are formed is occluded, the micropores are maintained for a long time (more than 72 hours), so that the drug contained in the support layer can be continuously delivered to the skin. The occlusive backing layer film is a semi-permeable film that allows water vapor, oxygen and carbon dioxide to pass through, is waterproof, and does not allow bacteria to penetrate. The film is a form that can be attached to the skin as acrylic adhesive is applied to films such as polyurethane, polyethylene, and nylon derivatives. Examples of the commercially available films having these characteristics include Tegaderm™ Film (3M), and Opsite™ Flexigrid and OpSite™ Flexifix (Smith & Nephew), but not always limited thereto. Another important role of the occlusive backing layer film is to prevent bacterial invasion from the outside, preventing the micropores formed by the microneedle from being contaminated by bacteria. In Examples to be described later, Tegaderm™ Film (3M) was used.

The microneedle patch provided in one aspect of the present invention may further include a protective layer to protect an adhesive layer before being used on the skin. In addition, the drug included in the microneedle and/or the support layer can be used as a transdermally absorbable formulation by applying not only chemical drugs (low molecular weight drugs) but also peptide or protein drugs.

The microneedle patch provided in one aspect of the present invention may have increased drug content per unit area (1 $cm^2$) to maximum of 100 mg unlike existing microneedles and thus has a higher drug content per unit area than an existing transdermal absorption agent, and is capable of delivering the drug into the body for a short time (within 24 hours) and a long time (approximately three days or more) via micropores formed by means of microneedles. This is supported by examples and experimental examples to be described later.

Hereinafter, the present invention will be described in detail by the following preparative examples, examples and experimental examples.

However, the following preparative examples, examples and experimental examples are only for illustrating the present invention, and the contents of the present invention are not limited thereto.

EXAMPLE

Preparation of Microneedle Patch

The microneedle patch system provided in one aspect of the present invention was manufactured by the following processes (1) to (8), and a schematic diagram illustrating a method of manufacturing the microneedle patch system according to the present embodiment is shown in FIG. 2.

(1): A microneedle master was prepared using a 3D printer or a microprocessor.

(2): A microneedle (female mold) was prepared using silicon (polydimethylsiloxane; FDMS).

(3): A polymer solution to be used for the microneedle unit and the high-dose drug support layer was prepared, and at this time, the polymer solution was prepared by including the drug together.

(4): To form the microneedle unit, a small amount of the polymer solution prepared in (3) was poured into the microneedle mold prepared in (2), and the solvent was dried.

(5): To form the high-dose drug support layer, the polymer solution prepared in (3) was poured into the microneedle mold of (4), and the solvent was dried.

(6): A drug-free biocompatible support was added on top of the drug support layer of (5) above.

(7): The needle unit was demolded so as not to be damaged.

(8): An airtight (occlusive) backing layer film was attached to the outside of the support formed in (6).

The polymer solution prepared in (3) above includes the following components,

Specific Example 1: Including donepezil as a drug (Example used in animal experiment)
Drug (donepezil hydrochloride) 5% (w/w)
Polymer (polyvinylpyrrolidone, PVP) 15% (w/w)
Saccharide (trehalose) 5% (w/w)
Solvent (distilled water, DW) 75% (w/w)

Specific Example 2: Including donepezil as a drug
Drug (donepezil hydrochloride) 8% (w/w)
Polymer (polyvinylpyrrolidone, PVP) 15% (w/w)
Saccharide (trehalose) 5% (w/w)
Solvent (distilled water, DW) 72% (w/w)

Specific Example 3: Including donepezil as a drug
Drug (donepezil hydrochloride) 2.5% (w/w)
Polymer (hyaluronic acid, HA) 1.0% (w/w)
Saccharide (trehalose) 1.5% (w/w)
Solvent (distilled water, DW) 95% (w/w)

Specific Example 4: Including celecoxib as a drug
Drug (celecoxib) 5% (w/w)
Polymer (polyvinylpyrrolidone, PVP) 15% (w/W)
PEG 400 5% (w/w)
Solvent (ethanol, EtOH) 75% (w/w)

Specific Example 5: Including insulin as a drug
Drug (insulin) 2.0% (w/w)
Polymer (hyaluronic acid, HA) 1.0% (w/w)
Saccharide (trehalose) 2.0% (w/w)
Solvent (distilled water, DW) 95% (w/w)

Specific Example 6: Including human growth hormone as a drug
Drug (human growth hormone, hGH) 2.0% (w/w)
Polymer (hyaluronic acid, HA) 1.5% (w/w)
Saccharide (trehalose) 1.58 (w/w)
Solvent (distilled water, DW) 95% (w/w)

Specific Example 7: Including teriparatide as a drug
Drug (teriparatide) 1.0% (w/w)
Polymer (hyaluronic acid, HA) 1.0% (w/w)
Saccharide (trehalose) 1.5% (w/w)
Solvent (distilled water, DW) 96.5% (w/w)

Specific Example 8: Including zolmitriptan as a drug
Drug (zolmitriptan) 1.08 (w/w)
Polymer (hyaluronic acid, HA) 1.0% (w/w)
Saccharide (maltose) 1.5% (w/w)
Solvent (distilled water, DW) 96.5% (w/w)

Specific Example 9: Including risedronate sodium as a drug
Drug (risedronate sodium) 1.0% (w/w)
Polymer (hyaluronic acid, HA) 1.0% (w/w)
Saccharide (trehalose) 2.0% (w/w)
Solvent (distilled water, DW) 96% (w/w)

Specific Example 10: Including donepezil as a drug
Drug (donepezil hydrochloride) 2.5% (w/w)
Polymer (sodium carboxymethyl cellulose, NaCMC) 1.0% (w/w)
Saccharide (sorbitol, SB) 1.5% (w/w)
Solvent (distilled water, DW) 95% (w/w)

Specific Example 11: Including donepezil as drug
Drug (donepezil hydrochloride) 2.5% (w/w)
Polymer (polyvinyl alcohol, PVA) 1.0% (w/w)
Saccharide (trehalose) 1.5% (w/w)
Solvent (distilled water, DW) 95% (w/w)

Specific Example 12: Including donepezil as a drug

Microneedle polymer solution

Drug (donepezil hydrochloride) 2.5% (w/w)

Polymer (hyaluronic acid, HA) 1.0% (w/w)

Saccharide (trehalose) 1.5%. (w/w)

Solvent (distilled water, DW) 95% (w/w)

Drug support layer polymer solution

Drug (donepezil hydrochloride) 8% (w/w)

Polymer (polyvinylpyrrolidone, PVP) 158 (w/w)

Saccharide (trehalose) 5% (w/w)

Solvent (distilled water, DW) 72% (w/w)

FIG. 3 shows the microneedle and the drug support layer prepared to contain 100 mg of donepezil hydrochloride according to Specific Example 1.

FIG. 4 shows the microneedle prepared to contain 10 mg of celecoxib according to Specific Example 4.

Experimental Example 1

Evaluation of Gelation Characteristics of a Solid Support Layer That Absorbs Moisture Evaporating From the Skin and Forms a Drug Reservoir In order to evaluate the gelation characteristics of the drug reservoir provided in one aspect of the present invention, the following experiment was performed.

After dissolving or dispersing a mixture of the following polymer materials and saccharides in a solvent, a film having a thickness of 0.5 mm was prepared using an automatic coating device (KP-3000, Gipae E&T Co., Ltd.), and the film was cut to have a width and length of 1 cm. The cut film was placed on the skin of the forearm and a Tegaderm™ film was attached thereon to determine whether gelation occurred after 1 hour. FIG. 5 shows the state of attaching a film made of a polymer material and saccharides to the skin (left) and the state of a gelated film after a certain period of time (right). FIG. 5 shows the shape of the film immediately after being attached to the skin (left) and the shape of the film gelated after a certain period of time (right).

Polymer Material Components:

hyaluronic acid (HA)

polyvinylpyrrolidone (PVP)

polyvinyl alcohol (PVA)

sodium carboxymethyl cellulose (NaCMC)

poloxamer (PX)

carbomer (CM)

hypromellose (HPMC)

hydroxypropyl cellulose (HPC)

hydroxyethyl cellulose (HEC)

sodium alginate (NaA)

ethyl cellulose (EC)

Saccharide Components:

trehalose (TH)

glycerin (GL)

propylene glycol (PG)

polyethylene glycol 400 (PEG)

sorbitol (SB)

The results are shown in Table 1 below.

TABLE 1

| | Polymer (%, w/w) | Saccharide (%, w/w) | Gelation |
|---|---|---|---|
| Prescription 1 | HA (30) | TH (70) | ○ |
| Prescription 2 | HA (40) | TH (60) | ○ |
| Prescription 3 | HA (60) | TH (40) | ○ |
| Prescription 4 | HA (80) | TH (20) | ○ |
| Prescription 5 | PVP (40) | TH (60) | ○ |
| Prescription 6 | PVP (60) | TH (40) | ○ |
| Prescription 7 | PVP (80) | TH (20) | ○ |
| Prescription 8 | PVP (80) | PEG (20) | ○ |
| Prescription 9 | PVP (85) | GL (15) | ○ |
| Prescription 10 | NaCMC (90) | TH (10) | ○ |
| Prescription 11 | PX (95) | TH (5) | ○ |
| Prescription 12 | CM (90) | TH (10) | ○ |
| Prescription 13 | HPMC (80) | PG (20) | ○ |
| Prescription 14 | HPC (85) | PEG (15) | ○ |
| Prescription 15 | HEC (70) | SB (30) | ○ |
| Prescription 16 | NaA (80) | SB (20) | ○ |
| Prescription 17 | EC (90) | TH (10) | x |
| Prescription 18 | EC (80) | TH (20) | x |

Experimental Example 2

Evaluation of Drug Release Characteristics of Microneedle Patch

In order to evaluate the drug release characteristics of the microneedle patch provided in one aspect of the present invention, the following experiment was performed.

More specifically, 3 mg/kg of donepezil was administered orally, 1 mg/kg of donepezil was administered subcutaneously, or 43 mg/kg of donepezil was administered using the microneedle patch prepared in the above example to rats, and the drug blood concentration patterns were compared. The results are shown in FIG. 6.

As shown in FIG. 6, in the case of the groups administered by oral administration and subcutaneous injection (control group), it was confirmed that the drug blood concentration was very low in about 1 day. On the other hand, it was found that the drug blood concentration was detected up to about 5 days (120 hours) when donepezil was administered using the microneedle patch prepared in the above example.

Next, rats were administered donepezil at different concentrations of 43 mg/kg, 80 mg/kg, and 125 mg/kg using the microneedle patch prepared in the above example, respectively, and the drug blood concentration patterns were compared. The results are shown in FIG. 7.

Figure 7:
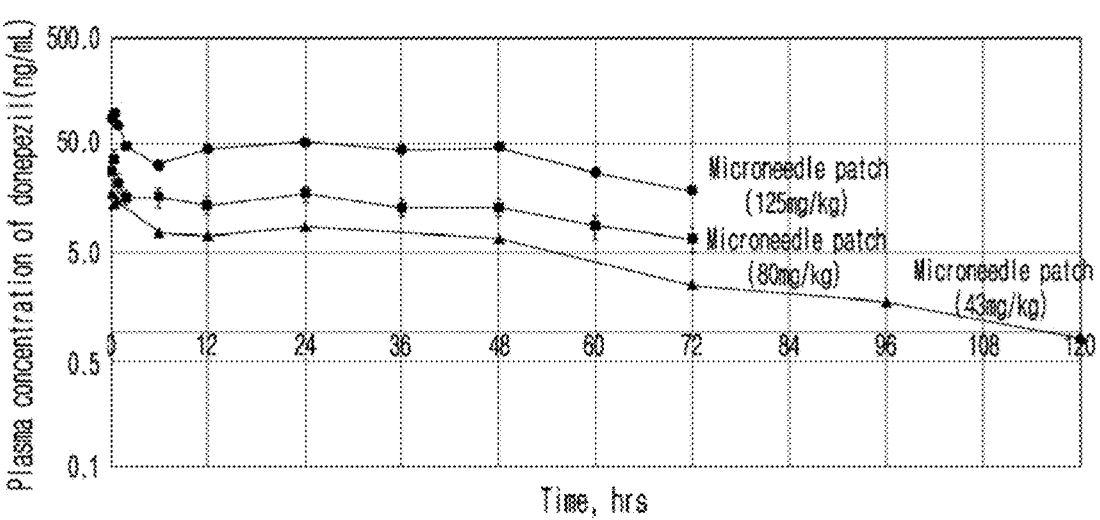
FIG. 7 is a graph showing the results of comparing the drug blood concentration patterns in rats after administration of donepezil using a microneedle patch prepared in an embodiment at the concentrations of 43 mg/kg, 80 mg/kg, and 125 mg/kg, respectively.

As shown in FIG. 7, it was found that the drug blood concentration increased in proportion to the administered concentration and could last for about 3 days or more.

Next, after administering 80 mg/kg of donepezil to rats using the microneedle patch prepared in the above example, the drug blood concentration pattern was compared between the case where the needle was removed in 1 hour and the case where the needle was applied for 3 days. The results are shown in FIG. 8.

Figure 8:
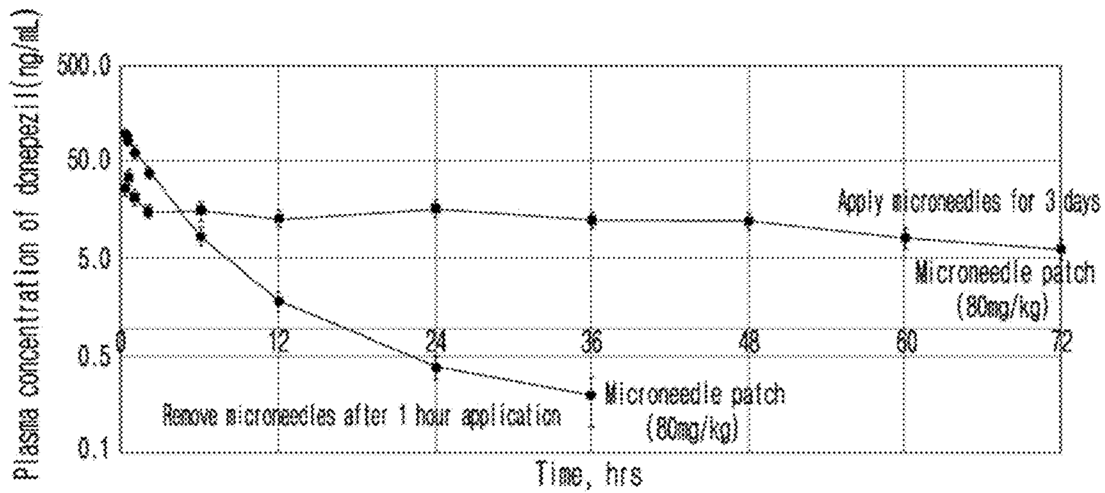
FIG. 8 is a graph showing the results of comparing the drug blood concentration patterns in rats after administration of 80 mg/kg of donepezil, when donepezil was removed after 1 hour of administration and when applied for 3 days.

As shown in FIG. 8, when the microneedle was removed in 1 hour, it was confirmed, that the drug concentration rapidly decreased in 36 hours. From the above results, it was found that in order to maintain the drug blood concentration at a specific level, the microneedle patch must be attached to the skin for a certain period of time and maintained.

What is claimed is:

1. A microneedle patch comprising the following components:

a microneedle comprising a drug;

a drug support layer supporting the microneedle on one surface and containing the drug;

a support provided in contact with a surface opposite to the surface of the drug support layer on which the microneedle is supported and not containing the drug; and an occlusive backing layer film provided in contact with a surface opposite to the surface of the support to which the drug support layer is in contact, wherein the occlusive backing layer film further includes an adhesive layer that covers the contact support surface and is configured to be extended to be directly attached to the skin, wherein the drug support layer containing the drug is configured to be gelated by moisture evaporated from the skin, wherein the occlusive backing layer film is moisture-proof to moisture evaporated from the skin, wherein the occlusive backing layer film is configured to prevent loss of moisture evaporated from the skin and thereby promote gelation of the drug support layer.

2. The microneedle patch according to claim 1, wherein the microneedle is configured to penetrates into the skin and is configured to release the drug as it dissolves within the skin.

3. The microneedle patch according to claim 1, wherein the microneedle is formed of a mixture of at least one selected from the group consisting of hyaluronic acid, polyvinylpyrrolidone (PVP), polyvinyl alcohol (PVA), sodium carboxymethyl cellulose, and saccharide.

4. The microneedle patch according to claim 3, wherein the saccharide is at least one selected from the group consisting of monosaccharides, disaccharides, and polysaccharides.

5. The microneedle patch according to claim 4, wherein the monosaccharide is at least one selected from the group consisting of fructose, galactose, glucose and mannose; the disaccharide is at least one selected from the group consisting of sucrose, lactose, maltose, trehalose, turanose and cellobiose; and the polysaccharide is at least one selected from the group consisting of dextran, diethylamino ethyl-dextran, dextrin, cellulose and β-glucans.

6. The microneedle patch according to claim 1, wherein the drug contained in the drug support layer is released due to the gelation of the drug support layer.

7. The microneedle patch according to claim 6, wherein the drug released due to the gelation of the drug support layer is configured to be absorbed into a body through the micropores in the skin formed by microneedles.

8. The microneedle patch according to claim 1, wherein the drug support layer is formed of a mixture of at least one selected from the group consisting of hyaluronic acid, polyvinylpyrrolidone (PVP), polyvinyl alcohol (PVA), sodium carboxymethyl cellulose (NaCMC), poloxamer, carbomer, hypromellose, hydroxypropyl cellulose (HPC), hydroxyethyl cellulose (HEC), sodium alginate, saccharide, glycerin, propylene glycol, polyethylene glycol 400, and sorbitol (SB).

9. The microneedle patch according to claim 1, wherein the occlusive backing layer film is configured to prevent loss of moisture evaporated from the skin, so that the micropores in the skin formed by the microneedle are kept open while the microneedle patch is attached to the skin.

10. The microneedle patch according to claim 9, wherein the micropores in the skin are configured to be maintained in an open state, and the drug released due to the gelation of the drug support layer is configured to be continuously absorbed into the skin.

11. The microneedle patch according to claim 1, wherein the microneedle patch further includes a protective layer to protect an adhesive layer before being used on the skin.

12. The microneedle patch according to claim 1, wherein the microneedle has one or more shapes selected from the group consisting of a circular cone shape, a quadrangular pyramid shape, and a triangular pyramid shape.

13. The microneedle patch according to claim 1, wherein the support is formed of at least one selected from the group consisting of biocompatible polymers, ceramics, and metals.

* * * * *